(12) United States Patent
Ngo et al.

(10) Patent No.: US 9,119,626 B2
(45) Date of Patent: Sep. 1, 2015

(54) METHOD FOR ASSEMBLING INTRODUCER SHEATH WITH AN EMBOLIC COIL DEVICE

(71) Applicant: Boston Scientific Scimed, Inc., Maple Grove, MN (US)

(72) Inventors: Tra Huong Ngo, San Jose, CA (US); Michael Williams, Dover, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/328,456

(22) Filed: Jul. 10, 2014

(65) Prior Publication Data

US 2014/0324096 A1     Oct. 30, 2014

Related U.S. Application Data

(63) Continuation of application No. 12/635,601, filed on Dec. 10, 2009, now Pat. No. 8,790,364.

(60) Provisional application No. 61/121,515, filed on Dec. 10, 2008.

(51) Int. Cl.
  *A61B 17/00* (2006.01)
  *A61B 17/12* (2006.01)
  *B21D 49/00* (2006.01)
  *B21D 9/00* (2006.01)
  *A61B 19/02* (2006.01)

(52) U.S. Cl.
  CPC ......... *A61B 17/1214* (2013.01); *A61B 17/1215* (2013.01); *A61B 17/12022* (2013.01); *A61B 17/12113* (2013.01); *A61B 17/12145* (2013.01); *B21D 9/00* (2013.01); *B21D 49/00* (2013.01); *A61B 19/026* (2013.01); *A61B 2017/00955* (2013.01); *A61B 2017/1205* (2013.01); *A61B 2017/12063* (2013.01)

(58) Field of Classification Search
  CPC ........ A61F 2/966; B21D 39/04; B21D 49/00; B21D 9/04; B21D 9/01; B21D 9/00; B21D 9/12; B21D 9/05; B21D 9/10; B21D 9/14; Y10T 29/49929; Y10T 29/49927; A61B 17/1214
  See application file for complete search history.

(56) References Cited

U.S. PATENT DOCUMENTS

| | | |
|---|---|---|
| 4,739,768 A | 4/1988 | Engelson |
| 5,238,004 A | 8/1993 | Sahatjian et al. |

(Continued)

FOREIGN PATENT DOCUMENTS

| | | |
|---|---|---|
| WO | 9930762 | 6/1999 |
| WO | 2004060464 | 7/2004 |
| WO | 2005107612 | 11/2005 |

OTHER PUBLICATIONS

All non-patent literature documents and foreign patent documents have been previously uploaded in parent U.S. Appl. No. 12/635,601, filed Dec. 10, 2009.

*Primary Examiner* — Jermie Cozart
(74) *Attorney, Agent, or Firm* — Seager, Tufte & Wickhem LLP

(57) ABSTRACT

Introducer sheaths for use with embolic coil devices and methods for making and using the same. An example introducer sheath assembly may include an introducer sheath having a proximal end, a distal end, and a body portion defined therebetween. The body portion may include two or more bends formed therein. An embolic coil device may be disposed within the introducer sheath.

14 Claims, 10 Drawing Sheets

(56) References Cited

U.S. PATENT DOCUMENTS

| | | |
|---|---|---|
| 5,389,090 A | 2/1995 | Fischell et al. |
| 5,522,836 A | 6/1996 | Palermo |
| 5,569,218 A | 10/1996 | Berg et al. |
| 5,603,705 A | 2/1997 | Berg et al. |
| 5,674,208 A | 10/1997 | Berg et al. |
| 5,680,873 A | 10/1997 | Berg et al. |
| 5,733,248 A | 3/1998 | Adams et al. |
| 5,772,609 A | 6/1998 | Nguyen et al. |
| 5,853,400 A | 12/1998 | Samson et al. |
| 5,860,963 A | 1/1999 | Azam et al. |
| 5,911,715 A | 6/1999 | Berg et al. |
| 6,139,510 A | 10/2000 | Palermo et al. |
| 6,344,041 B1 | 2/2002 | Kupiecki et al. |
| 6,508,803 B1 | 1/2003 | Horikawa et al. |
| 6,685,722 B1 | 2/2004 | Rosenbluth et al. |
| 6,866,665 B2 | 3/2005 | Orbay |
| 6,974,436 B1 | 12/2005 | Aboul-Hosn et al. |
| 7,367,980 B2 | 5/2008 | Kida et al. |
| 2004/0045645 A1 | 3/2004 | Zhou |
| 2005/0064124 A1 | 3/2005 | Wang et al. |
| 2005/0075625 A1 | 4/2005 | Dao et al. |
| 2005/0080356 A1 | 4/2005 | Dapolito et al. |
| 2006/0036280 A1 | 2/2006 | French et al. |
| 2006/0264904 A1 | 11/2006 | Kerby et al. |
| 2006/0271149 A1 | 11/2006 | Berez et al. |
| 2006/0282112 A1 | 12/2006 | Griffin |
| 2007/0083219 A1 | 4/2007 | Buiser et al. |
| 2007/0142859 A1 | 6/2007 | Buiser et al. |
| 2007/0142893 A1 | 6/2007 | Buiser et al. |
| 2007/0270903 A1 | 11/2007 | Davis, III et al. |
| 2008/0082176 A1 | 4/2008 | Slazas |
| 2008/0097462 A1 | 4/2008 | Mitelberg et al. |

METHOD FOR ASSEMBLING INTRODUCER SHEATH WITH AN EMBOLIC COIL DEVICE

CROSS-REFERENCE TO RELATED APPLICATIONS

This application is a continuation of U.S. application Ser. No. 12/635,601, filed Dec. 10, 2009, now U.S. Pat. No. 8,790,364 B2 which claims the benefit of U.S. Provisional Application No. 61/121,515, filed Dec. 10, 2008, the entire disclosures of which are incorporated herein by reference.

FIELD OF THE INVENTION

The present invention pertains to introducer sheaths for use with an embolic coil device. More particularly, the present invention pertains to design, material, manufacturing method, packaging, and use alternatives for introducer sheaths, embolic coil and introducer sheath assemblies, and kits.

BACKGROUND

A wide variety of introducer sheaths have been developed for medical use including, for example, aiding in the delivery of an embolic coil device. These introducer sheaths are manufactured, packaged, and used according to any one of a variety of different methods. Of the known introducer sheaths and methods, each has certain advantages and disadvantages. There is an ongoing need to provide alternative introducer sheaths as well as alternative methods for manufacturing, packaging, and using introducer sheaths.

BRIEF SUMMARY

The invention provides design, material, manufacturing method, packaging, and use alternatives for introducer sheaths, embolic coil and introducer sheath assemblies, kits, and the like. An example introducer sheath assembly may include an introducer sheath having a proximal end, a distal end, and a body portion defined there between. The body portion may include two or more bends formed therein. An embolic coil device may be disposed within the introducer sheath.

An example method for packaging an embolic coil device and introducer sheath assembly may include providing an elongate mandrel, providing an introducer sheath, disposing the mandrel within the introducer sheath, softening the introducer sheath, removing the mandrel from the introducer sheath, loading an embolic coil device within the introducer sheath, and disposing the introducer sheath within a dispenser coil. The mandrel may have one or more bends formed therein.

An example introducer sheath kit may include a dispenser coil, an introducer sheath disposed in the introducer coil, and an embolic coil device disposed within the introducer coil. The introducer sheath may include one or more pre-formed bends and a flared proximal end region.

An example method for treating an aneurysm may include providing an introducer sheath assembly including an introducer sheath and an embolic coil device disposed within the introducer sheath, providing a catheter, advancing the catheter through the vasculature to a position adjacent an aneurysm, attaching the introducer sheath to the catheter, advancing the embolic coil device from the introducer sheath into the catheter and toward the aneurysm, and disposing a portion of the coil device at the aneurysm. The introducer sheath may have one or more bend formed therein and a flared proximal end region.

Another example method for packaging an embolic coil device and introducer sheath assembly may include providing an introducer sheath, arranging the introducer sheath in a curved configuration by disposing the sheath about a series of pins, softening the introducer sheath, removing the introducer sheath from the pins, loading an embolic coil device within the introducer sheath, and disposing the introducer sheath within a dispenser coil.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
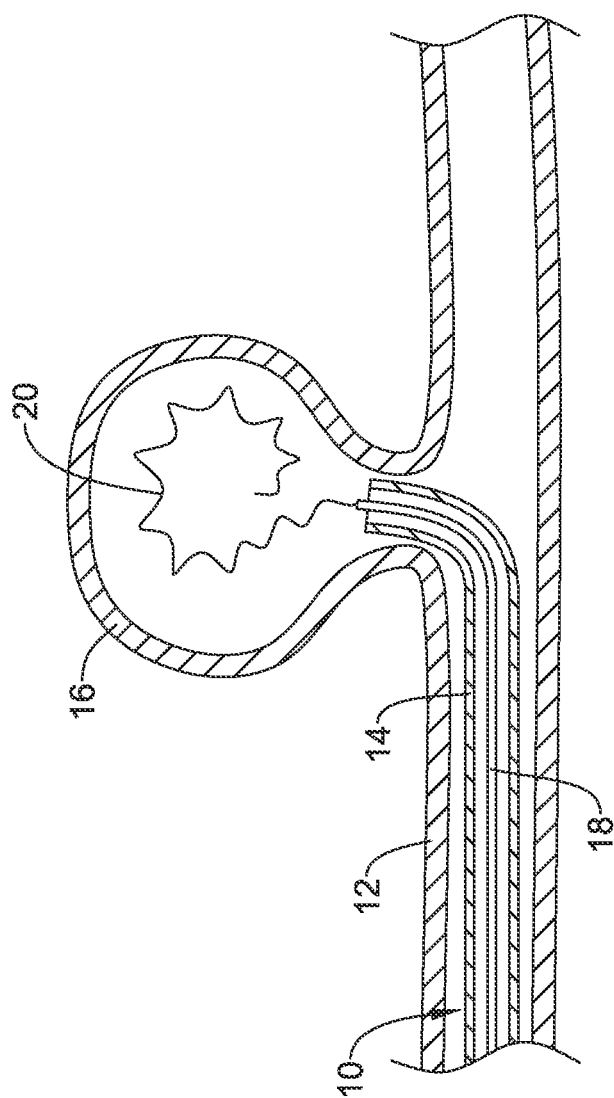
FIG. 1 is a plan view of an example embolic coil device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. Any feature of any example embodiment may be incorporated into any other embodiment, as appropriate, unless clearly stated to the contrary.

FIG. 1 is a plan view of an example medical device 10, for example an embolic coil assembly, disposed in a blood vessel 12. Assembly 10 may include a catheter 14 that may be generally configured for advancing within the anatomy of a patient to a position adjacent an area of interest, for example, an aneurysm 16. Catheter 14 may resemble catheters used in the art and they may be sized for the appropriate intervention. As such, it should be understood that there may be a broad range of possible catheter and catheter shaft constructions that may be used. For example, if catheter 14 is intended to treat aneurysm 16 in the neurovasculature, catheter 14 may be appropriately sized to effectively access the neurovasculature. Some examples of suitable catheter and catheter shaft constructions can be found in U.S. Pat. Nos. 5,569,218, 5,603,705, 5,674,208, 5,680,873, 5,733,248, 5,853,400, 5,860,963, 5,911,715, and 6,866,665, the entire disclosures of which are all herein incorporated by reference. Some additional examples of suitable catheter and catheter shaft constructions can be found in U.S. Patent Application Pub Nos. US 2004/0045645 and 2006/0282112, the entire disclosures of which are all herein incorporated by reference.

Figure 2:
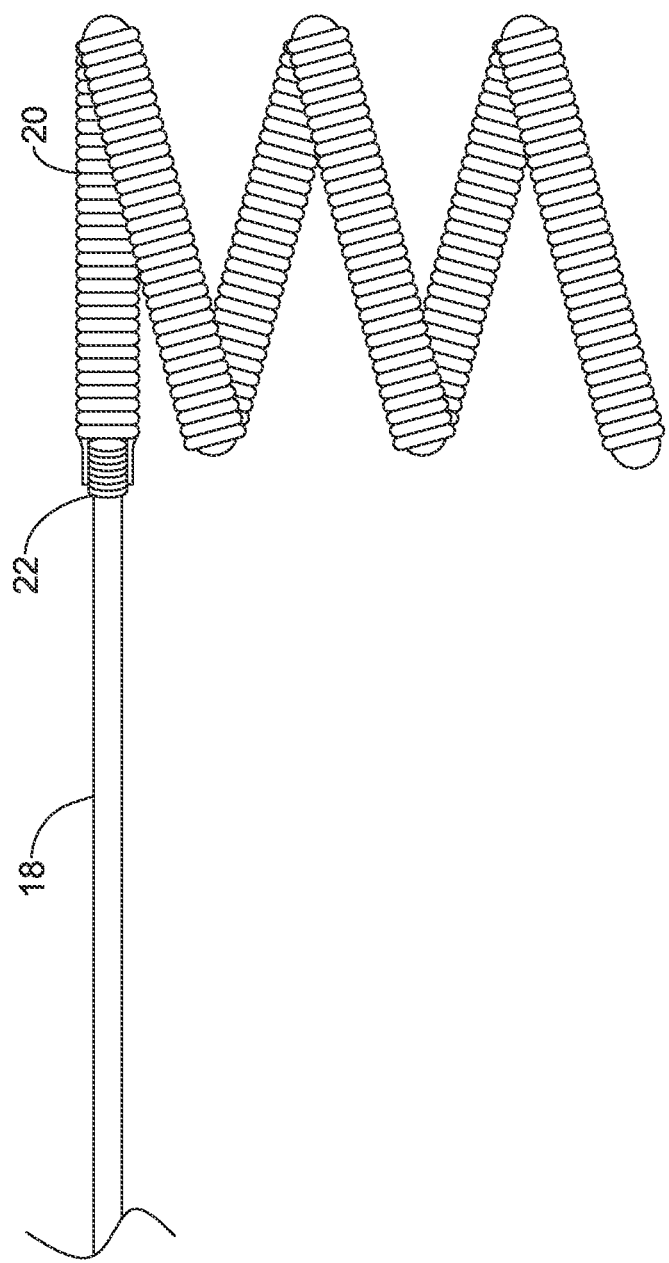
FIG. 2 is a side view of an example embolic coil device.

Assembly 10 may include an embolic coil device or other device that may be used to diagnose and/or treat aneurysm 16. The embolic coil device may include an occlusion device or embolic coil 20 that may be coupled to a delivery or push wire 18 by, for example, a sacrificial link 22 as shown in FIG. 2. Delivery wire 18 may typically having a diameter of about 0.010 inch to about 0.020 inch (0.254-0.508 mm) and may have a length of about 50 cm to about 300 cm. Delivery wire 18 may have a substantially constant outer diameter or it may include one or more tapers. Delivery wire 18 may be formed of any suitable material including any of those listed herein. In some embodiments, delivery wire 20 may be coated with a lubricious coating (not shown), which may reduce friction during delivery of occlusion device 20.

In at least some embodiments, occlusion device 20 may take the form of an embolic coil that may be configured to be disposed in and treat, for example, an aneurysm such as aneurysm 16. Embolic coil 20 may be similar to other similar embolic coils. For example, embolic coil 20 may be about 1 to about 50 cm in length it may have a sufficient flexibility such that embolic coil 20 may be capable of deforming and folding and/or bending within a vascular cavity such as aneurysm 16. Embolic coil 20 may be pliable and its overall shape may be easily deformed. For example, when inserted into catheter 14, embolic coil 20 may be easily straightened to lie axially within the lumen of catheter 14. Once disposed outside of or advanced out from the distal tip of catheter 14, embolic coil 20 may convert into a more shapely, nonlinear form such as shown in FIG. 2, and may be loosely deformed to the interior shape of a vascular cavity. Embolic coil 20 may be formed of any suitable material including any of those listed herein. Additionally, embolic coil 20, or a portion thereof, may be coated with a thrombogenic agent, a drug or medication, a biological agent, and the like, or any other suitable coating.

Sacrificial link 22 may be a discrete element disposed between embolic coil 20 and delivery wire 18 that may be oxidized and/or dissipated to allow embolic coil 20 to be separated from delivery wire 18 at the desired time. Sacrificial link 22 may be oxidized and/or dissipated in any suitable manner. For example, an electrical current may be passed through delivery wire 20 to initiate an electrolytic process at link 22 while submerged in a conductive fluid medium such as a bloodstream of a vessel. During electrolysis, sacrificial link 22, or a portion thereof, may be oxidized and dissipated, thus decoupling embolic coil 20 from delivery wire 18. Some additional detail regarding delivery wire 18, embolic coil 20, and sacrificial link 22 may be found in U.S. Patent Application Pub No. US 2006/0282112, the entire disclosure of which is herein incorporated by reference.

Figure 3:
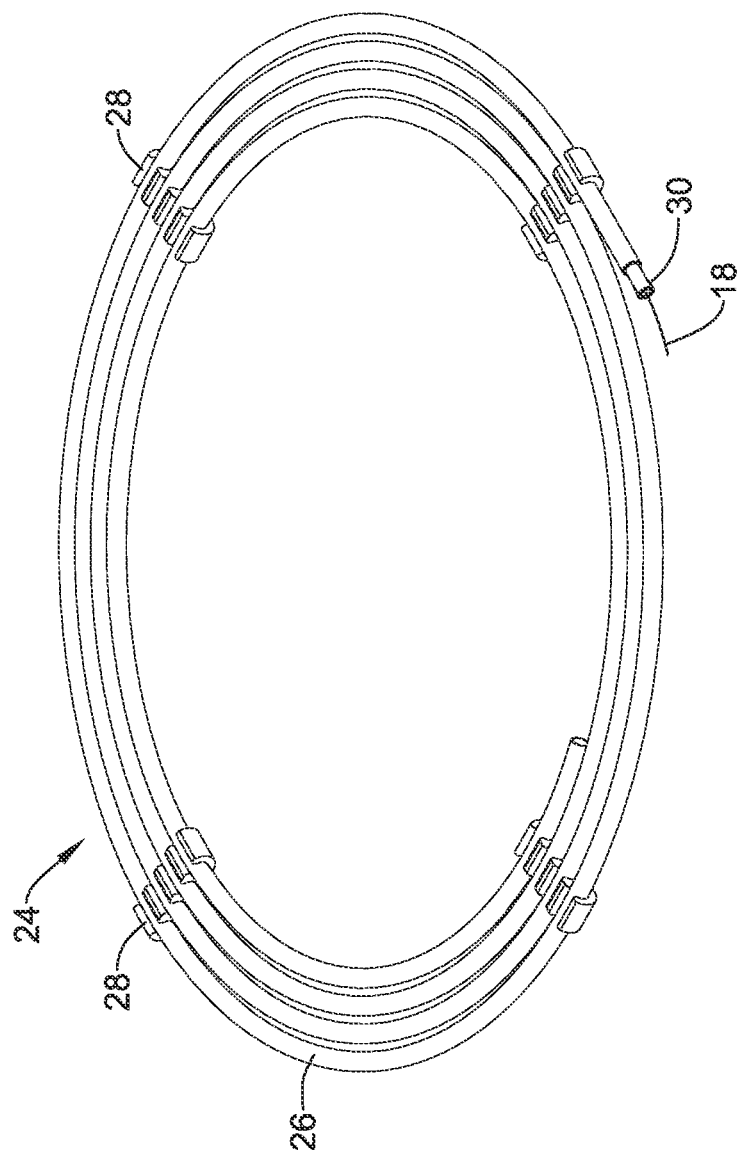
FIG. 3 is a side view of an example dispenser coil.
Figure 4:
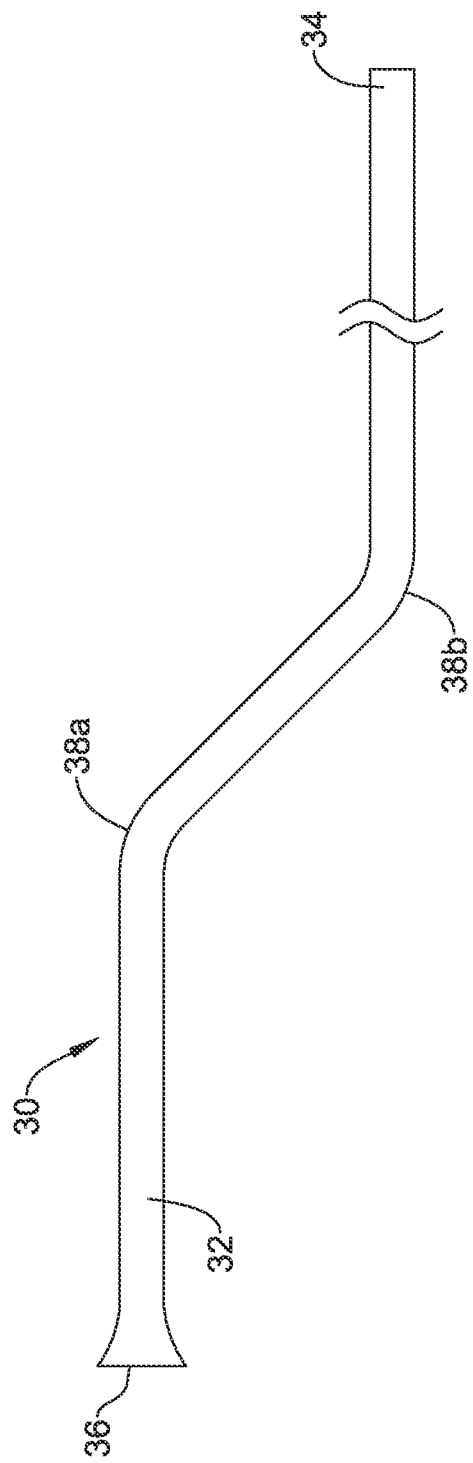
FIG. 4 is a side view of an example introducer sheath.

The process of delivering embolic coil 20 to the appropriate portion of the anatomy may include attaching an introducer sheath 30 (which may also be part of assembly 10 and/or the embolic coil device, is shown in FIGS. 3-4, and is discussed in more detail below) to the proximal end of catheter 14, the later being available adjacent to an appropriate vascular access site such as to adjacent the femoral artery. Introducer sheath 30 may function as both a "holding device" that may hold the embolic coil device in a convenient manner or configuration (e.g., a low profile configuration) until needed for use and a "delivery device" that facilitates the delivery of the embolic coil device to the appropriate portion of the anatomy at the desired time (e.g., via catheter 14). Because introducer sheath 30 may be a part of the embolic coil device, introducer sheath 30 may be packaged together with delivery wire 18 and embolic coil 20 and/or form an embolic coil device assembly.

At least a portion of delivery wire 18 and embolic coil 20, which may be held in a collapsed or reduced profile configuration, may be disposed within introducer sheath 30. When introducer sheath 30 is properly associated with (e.g., abutting) and/or attached to catheter 14, embolic coil 20 can be advanced out from introducer sheath 30 and into catheter 14, for example, by distally advancing wire 20, and then further advanced within catheter 14 and, ultimately, out from catheter 14 when disposed at the appropriate target site (e.g., within aneurysm 16). Once properly positioned within the target site, sacrificial link 22 may be dissipated to release embolic coil 20 from delivery wire 18 so that embolic coil 20 may be disposed and left in the appropriate portion of the anatomy (e.g., at or adjacent aneurysm 16) and catheter 14 and delivery wire 18 may be removed from the anatomy.

When devices such as introducer sheath 30, delivery wire 18, and embolic coil 20 are sold to the appropriate medical professionals and medical facilities, they may be packaged in way that is convenient for both the seller and the purchaser. For example, the devices may be packaged in a dispenser coil 24 that allows a relatively long and thin object (e.g., introducer sheath 30, delivery wire 18, coil 20, etc.) to be conveniently held in a manageably sized container as illustrated in FIG. 3. Accordingly, dispenser coil 24 may be a portion of the packaging for the embolic coil device (e.g., delivery wire 18 and/or coil 20). Dispenser coil 24 may also be used to package other components of assembly 10 including, for example, catheter 14. In addition, dispenser coil 24 may also be further packaged in a suitable pouch or bag that may allow dispenser coil 24 and any objects disposed therein to be properly sterilized (and to be kept sterilized). This may form a medical device package or kit that is suitable for sale to the appropriate medical professionals.

As the name implies, dispenser coil 24 may include a tubular member 26 that is wrapped in a coiled configuration. To hold dispenser coil 24 in the coiled configuration, one or more holding members or clips 28 may be used. Clips 28 may be secured to one or more windings of dispenser coil 24 and hold the windings together, as appropriate. The use of dispenser coil 24 may allow for the desirably compact packaging of introducer sheath 30, delivery wire 18, and embolic coil 20 that is convenient for medical professionals during use and convenient for the storage, transportation, and holding of sheath 30, delivery wire 18, and embolic coil 20.

Introducer sheath 30 may be disposed in dispenser coil 24. Embolic coil 20 and delivery wire 18 may be disposed in introducer sheath 30, as appropriate, for packaging, transportation, and sale of such. Because embolic coil 20 may be collapsed or otherwise in a reduced profile configuration while disposed within introducer sheath 30, and because embolic coil 20 may expand to a larger configuration once it emerges from sheath 30, it may be desirable for the position of embolic coil 20 and/or delivery wire 18 to be longitudinally stabilized or secured within sheath 30. This may be because, for example, if embolic coil 20 emerged out from introducer sheath 30 earlier than desired, it may expand to a size that may make it difficult for coil 20 to be easily reloaded into sheath 30 or catheter 14, or otherwise used in a practical manner.

Introducer sheath 30 may include one or more design features that may help to longitudinally stabilize the position of embolic coil 20 and/or delivery wire 18 therein. For example, sheath 30 may include a body or body portion that has one or more bends or curves formed therein such as a bend 38*a* and a bend 38*b* as shown in FIG. 4. In this example, bends 38*a*/38*b* are arranged to bend downward and then straighten sheath 30, respectively. As a portion of the embolic coil device (e.g., delivery wire 18 and coil 20), which may otherwise be configured to be substantially straight, extends through bends 38*a*/38*b*, wire 18 and/or coil 20 may be held in place by friction forces that occur between sheath 30 and wire 18 (and/or coil 20). In general, the friction forces created by bends 38*a*/38*b* may be sufficient to hold the position of coil 20 and wire 18 relative to sheath 30 yet not so large as to cause damage, deformation, or other undesirable effects on coil 20 and/or wire 18.

Furthermore, bends 38*a*/38*b* may exert the same friction forces on coil 20 and/or wire 18 when the embolic coil device is disposed within the dispenser coil 24. This may be true even when the shape or configuration of introducer sheath 30 is altered such as when it is disposed in dispenser coil 24. Thus, bends 38*a*/38*b* allow for the embolic coil device to be packaged within dispenser coil 24 while maintaining the position of wire 18 and/or coil 20 within introducer sheath 30. In some embodiments, introducer sheath 30 may also include a twisted region (not shown) that may additionally help to hold the position of wire 18 and coil 20 by clamping down onto wire 18 and/or coil 20. Prior to use, the twisted region may need to be "untwisted" by the clinician. Because this may add an additional step to the intervention, it may be desirable for sheath 30 to be free of any twisted regions. Therefore, at least some embodiments of sheath 30 are free of twisted regions.

FIG. 4 illustrates some additional features of introducer sheath 30. For example, introducer sheath 30 may include a proximal portion 32 and a distal portion 34. Proximal portion 32 may include a flared proximal end 36. Flared end 36 may be desirable for a number of reasons. For example, flared end 36 may facilitate loading, prevent catching of other devices on the end of sheath 30, aid in identifying and locating proximal end 36, etc. In some embodiments, distal portion 34 may be tapered.

The form and configuration of the bend 38*a*/38*b* can vary considerably in several embodiments as many different curved shapes are contemplated. For example, the number of curves or bends may vary to include one, two, three, four, five, six, or more (e.g., multiple) bends. These bends may vary in radius of curvature, arclength of the curve, direction of the curve or bend, and the like. The bends may be regular in shape, irregular in shape, or combinations thereof. In addition, the spacing between the bends may also vary. In at least some embodiments, all the bends in a given introducer sheath may fall within a single plane (e.g., the bends are "two dimensional"). In other embodiments, one or more bends may lie outside the plane (e.g., the bends are "three dimensional"). It can be appreciated that a vast array of bend configurations can be utilized without departing from the spirit of the invention.

Bends 38*a*/38*b* may also be described as being "pre-formed". A pre-formed bend may be understood to be a bend that is designed to be present in an object when the object is not subjected to lateral or other bending forces (e.g., the object is "at rest"). The pre-formed bends differ from bends that may exist when a relatively flexible object such as introducer sheath 30 is bent or otherwise deformed into a non-linear shape.

Figure 5:
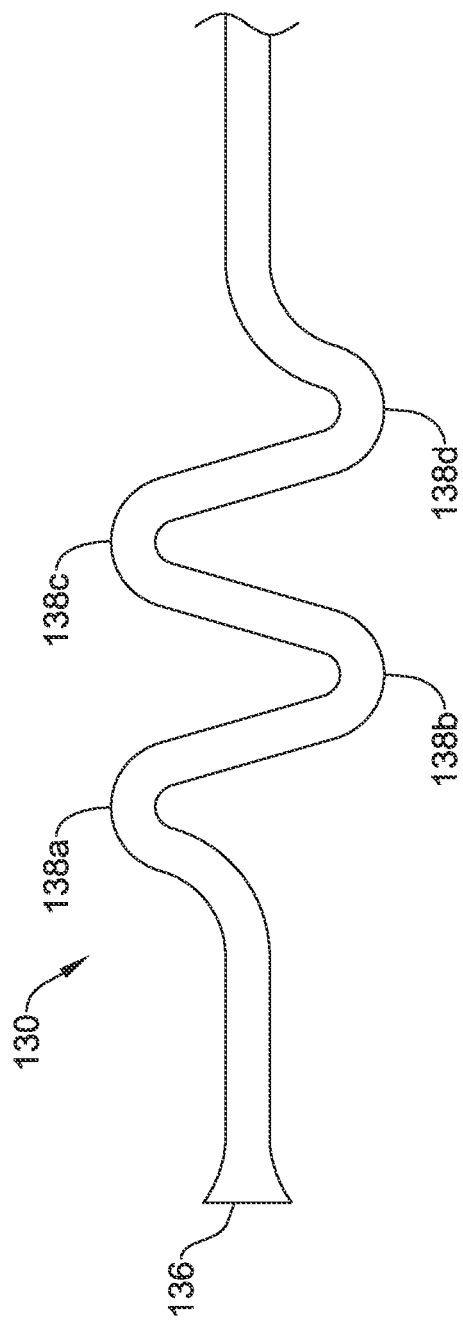
FIG. 5 is a side view of another example introducer sheath.
Figure 6:
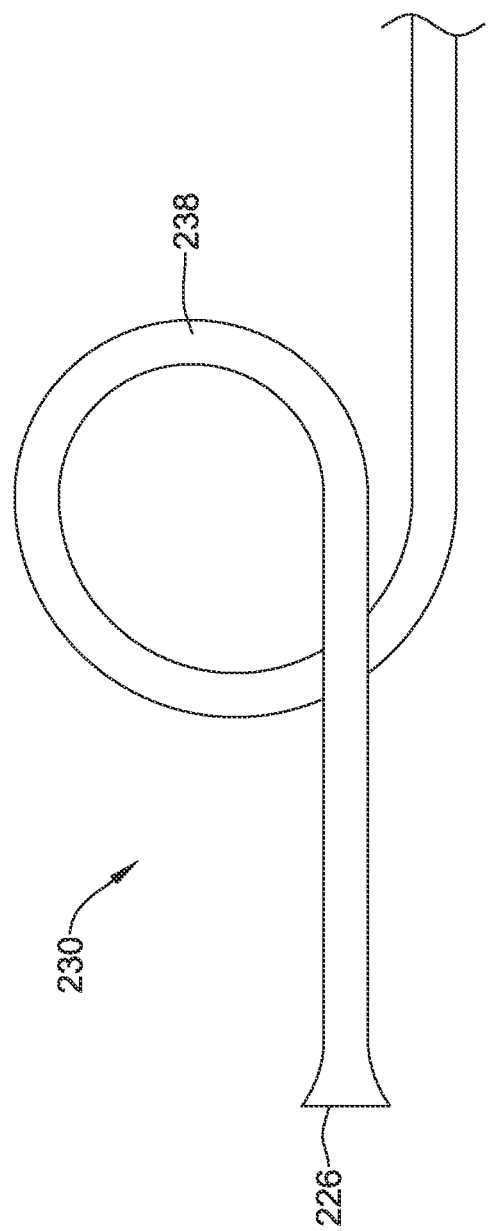
FIG. 6 is a side view of another example introducer sheath.
Figure 7:
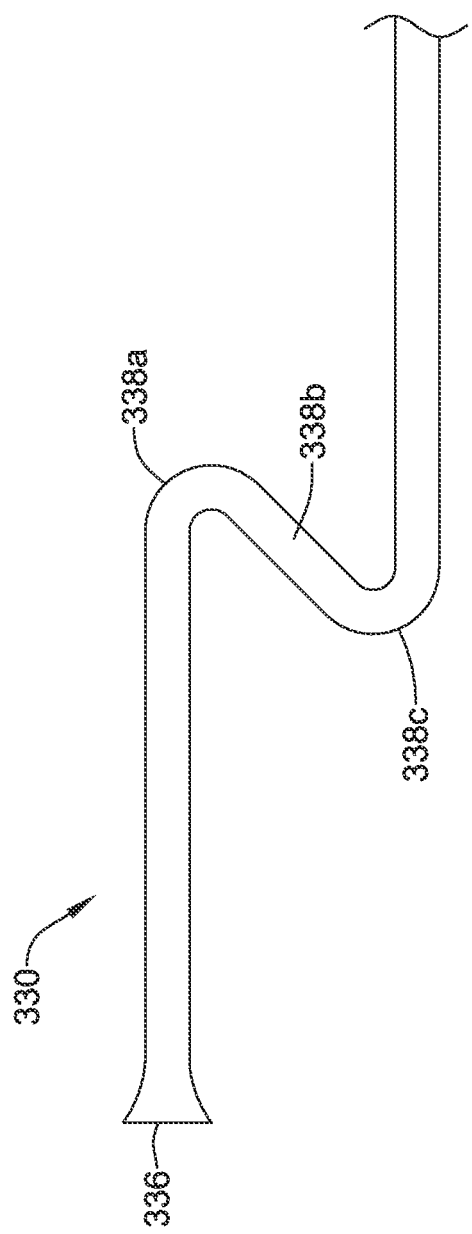
FIG. 7 is a side view of another example introducer sheath.
Figure 8:
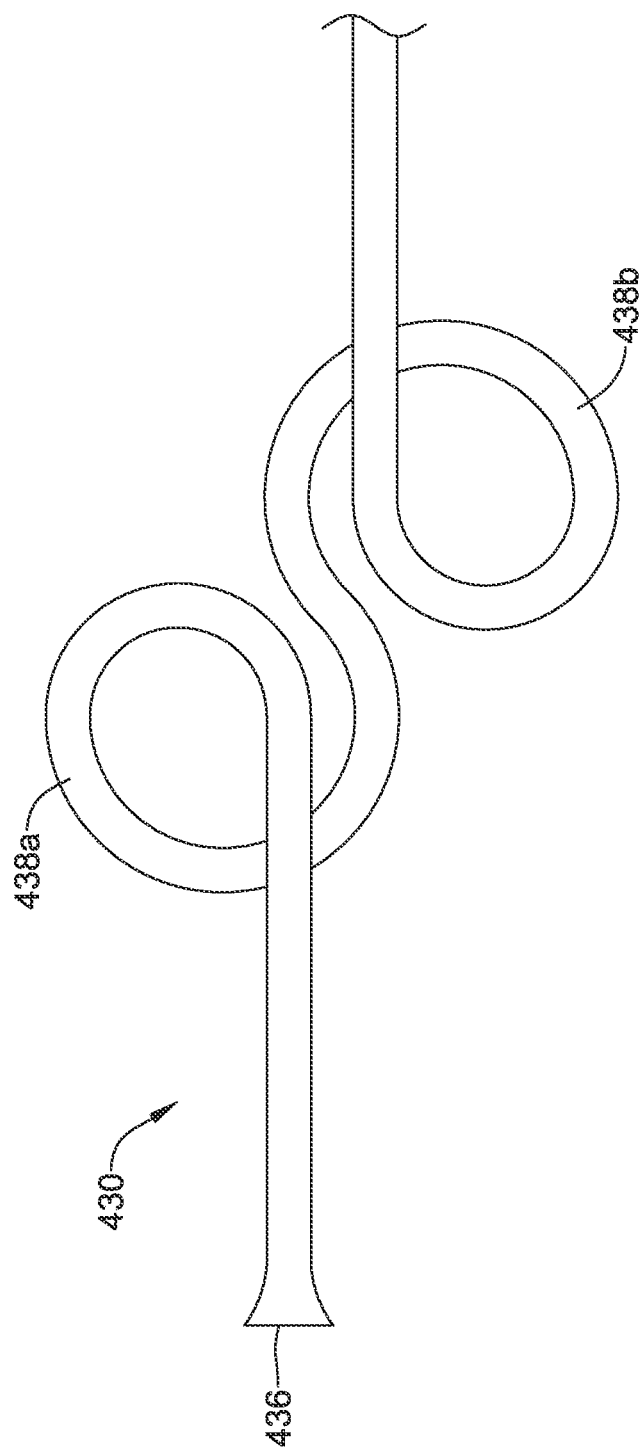
FIG. 8 is a side view of another example introducer sheath.

FIGS. 5-8 illustrate some of the example bend and/or curve configurations that are contemplated for example introducer sheaths. For example, FIG. 5 illustrates introducer sheath 130 having flared proximal end 136 and bends 138*a*/138*b*/138*c*/138*d*. Here it can be seen that bends 138*a* and 138*b* are oriented in opposing directions. Likewise, bends 138*c* and 138*d* are oriented in opposing directions. Bends 138*a* and 138*c* may be oriented in similar directions. Likewise, bends 138*b* and 138*d* may be oriented in similar directions. FIG. 6 illustrates introducer sheath 230 having flared proximal end 236 and loop portion 238. Loop portion 238 may include a series of bends that collectively form a complete loop. Thus, sheath 230 may be understood to include a plurality of bends and/or a complete loop. FIG. 7 illustrates introducer sheath 330 having flared proximal end 336, bend 338*a*, portion 338*b*, and bend 338*c*. In this example, portion 338*b* may extend proximally (e.g., toward end 336). Finally, FIG. 8 illustrates introducer sheath 430 having flared proximal end 436, loop portion 438*a*, and loop portion 438*b*.

Figure 9:
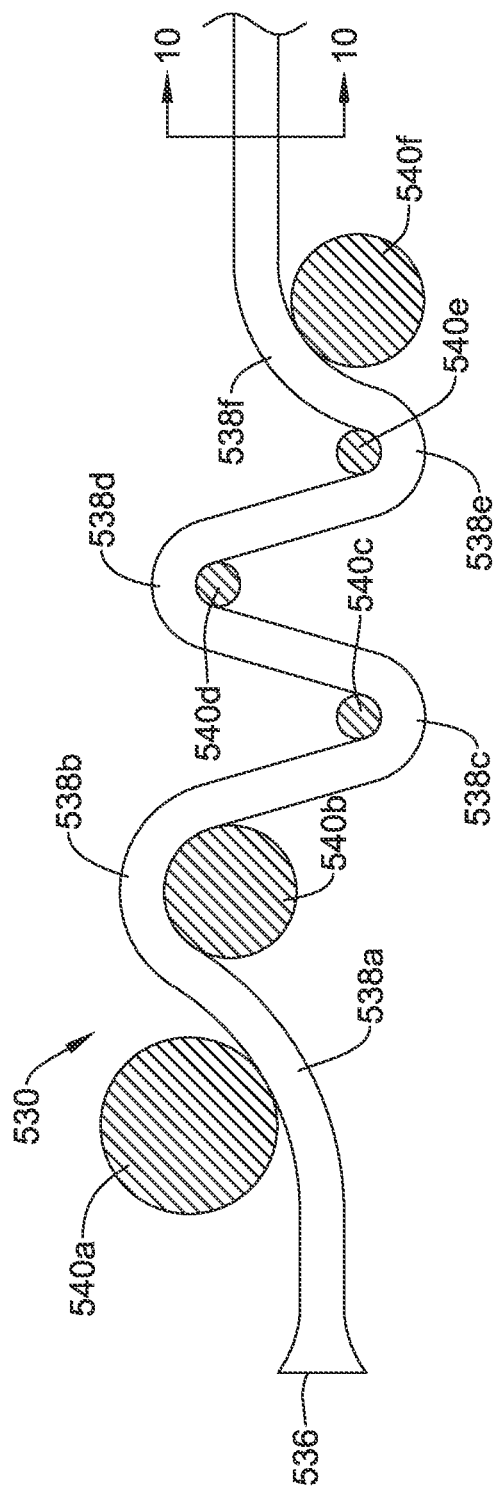
FIG. 9 is a side view of another example introducer sheath, which illustrates and example method for manufacturing an introducer sheath.

FIG. 9 illustrates an example method for manufacturing an introducer sheath in accordance with the spirit of the invention. Introducer sheath 530 may be arranged in the desired curved or bent configuration by disposing sheath 530 about a series of pins or rollers that may help define a series of bends in sheath 530 by holding sheath 530 in the desired shape. For example, sheath 530 may be disposed about pin 540*a* to define bend 538*a*, about pin 540*b* to define bend 538*b*, about pin 540*c* to define bend 538*c*, about pin 540*d* to define bend 538*d*, about pin 540*e* to define bend 538*e*, and about pin 540*f* to define bend 538*f*.

Once properly configured, sheath 530 may be softened to set the shape thereof (including the desired bends). In some embodiments, softening may include heating, melting, or both. The amount of heating/softening time, the heating/softening temperature, etc. may vary depending on the material composition, thickness, and geometry of sheath 530.

Figure 10:
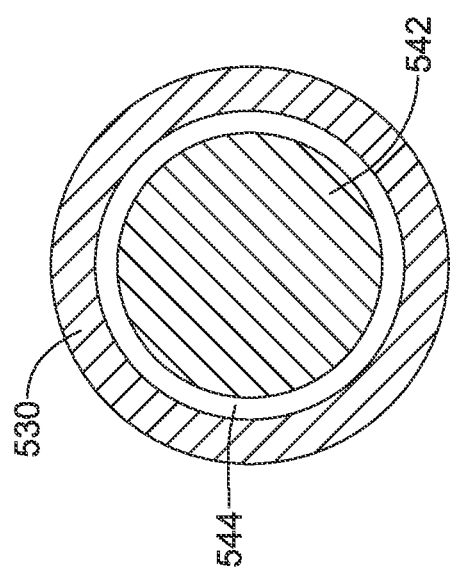
FIG. 10 is a cross-sectional view taken through line 10-10 in FIG. 9.

In some embodiments, a mandrel 542 may be disposed in the lumen 544 of sheath 530 during heating so as to preserve the shape of lumen 544 as illustrated in FIG. 10. In other embodiments, mandrel 542 may be preformed so as to include a plurality of bends so that introducer sheath 530 can be formed into the desired shape by disposing it over mandrel 542. Once over mandrel 542, sheath 530 can be softened so that it shifts from a non-shaped configuration to a shaped configuration that has one or more bends that correspond to bends formed in mandrel 542. Subsequently, sheath 530 may be re-hardened or re-solidified (e.g., when softening includes melting or partial melting) so that it maintains the shaped configuration. The use of a pre-shaped mandrel 542 may allow sheath 530 to be formed into the desired shape without the need of pins.

Once the shape of introducer sheath 530 is set, mandrel 530 may be removed from sheath 530. Subsequently, the embolic coil device (e.g., wire 18 and coil 20) may be loaded into sheath 530 and sheath 530 may be loaded or otherwise disposed in dispenser coil 24.

Manufacturing introducer sheath 530 may also include forming flared proximal end 536. This may include the use of a suitably formed mandrel. Alternatively, mandrel 542 may include the desired flared shape. In still other embodiments, flared end 536 may be formed with a hot soldering iron tip or simply by heating end 536 with, for example, an air jet.

The materials that can be used for the various components of assembly 10 (and/or other assemblies or components thereof) and the introducer sheaths disclosed herein may include those commonly associated with medical devices. For simplicity purposes, the following discussion makes reference to introducer sheath 30. However, this is not intended to limit the invention as the discussion may be applied to other structures or components of assembly 10 and/or any other suitable devices disclosed herein.

Sheath 30 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or sheath 30 may also be doped with, made of, or otherwise include a radiopaque material. Radiopaque materials are understood to be materials capable of producing a relatively bright image (e.g., and/or otherwise a contrasted image) on a fluoroscopy screen or another imaging technique during a medical procedure. This relatively bright image aids the user of sheath 30 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of sheath 30 to achieve the same result.

In some embodiments, a degree of MRI compatibility is imparted into sheath 30. For example, to enhance compatibility with Magnetic Resonance Imaging (MRI) machines, it may be desirable to make sheath 30 in a manner that would impart a degree of MRI compatibility. For example, sheath 30 may be made of a material that does not substantially distort the image and create substantial artifacts (artifacts are gaps in the image). Certain ferromagnetic materials, for example, may not be suitable because they may create artifacts in an MRI image. Sheath 30 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be utilized for sheath 30 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the polymer can contain up to about 6% LCP.

Introducer sheath 30 may also include a coating or covering (not shown). The covering or coating may be disposed along the interior of sheath 30, along the exterior of sheath 30, or both. The covering may be made from a polymer (including any of those listed above) or any other suitable material. In some embodiments, the covering may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or covering may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of assembling a medical device, the method comprising:
    forming two or more bends in a proximal portion of an introducer sheath; and
    disposing an embolic coil within the introducer sheath such that the embolic coil extends within the two or more bends formed in the proximal portion of the introducer sheath, wherein at least a portion of the embolic coil frictionally engages the two or more bends so as to secure the embolic coil within the proximal portion of the introducer sheath.

2. The method of claim 1, further comprising loading the introducer sheath including the embolic coil disposed therein within a dispenser coil.

3. The method of claim 1, wherein forming the two or more bends in the proximal portion of the introducer sheath comprises disposing a mandrel having two or more bends formed therein within the introducer sheath, softening the introducer sheath, and removing the mandrel from the introducer sheath.

4. The method of claim 1, wherein forming the two or more bends comprises disposing the introducer sheath about a plurality of pins to provide a curved configuration having two or more bends, softening the introducer sheath, and removing the introducer sheath from the plurality of pins.

5. The method of claim 1, wherein the embolic coil is coupled to a delivery wire by a sacrificial link.

6. The method of claim 1, further comprising flaring a proximal end of the introducer sheath.

7. A method of assembling a medical device comprising, the method comprising:
    disposing an elongate mandrel having two or more bends within a proximal portion of an introducer sheath;
    softening the proximal portion of the introducer sheath such that the introducer sheath conforms to the mandrel to form two or more bends;
    removing the mandrel from the introducer sheath; and
    loading an embolic coil within the introducer sheath such that at least a portion of the embolic coil extends within the proximal portion of the introducer sheath including the two or more bends such that the embolic coil is secured within the introducer sheath.

8. The method of claim 7, further comprising flaring a proximal end of the introducer sheath.

9. The method of claim 7, further comprising disposing the introducer sheath including the embolic coil within a dispenser coil.

10. The method of claim 7, wherein softening the introducer sheath includes heating the proximal portion of the introducer sheath.

11. The method of claim 7, wherein softening the introducer sheath includes melting the proximal portion of the introducer sheath.

12. The method of claim 7, wherein the embolic coil is coupled to a delivery wire via a sacrificial link.

13. The method of claim 7, wherein the introducer sheath includes polypropylene.

14. The method of claim 7, wherein the introducer sheath is free of a twisted region.

* * * * *